US00PP27159P3

(12) United States Plant Patent
Ilsink

(10) Patent No.: US PP27,159 P3
(45) Date of Patent: Sep. 20, 2016

(54) SHRUB ROSE PLANT NAMED 'INTROS01'

(50) Latin Name: *Rosa hybrida*
Varietal Denomination: IntRos01

(71) Applicant: Robert Ilsink, Leersum (NL)

(72) Inventor: Robert Ilsink, Leersum (NL)

(73) Assignee: Interplant Roses B.V. (NL)

( * ) Notice: Subject to any disclaimer, the term of this patent is extended or adjusted under 35 U.S.C. 154(b) by 110 days.

(21) Appl. No.: 14/120,794

(22) Filed: Jun. 27, 2014

(65) Prior Publication Data

US 2015/0382527 P1 Dec. 31, 2015

(51) Int. Cl.
*A01H 5/02* (2006.01)

(52) U.S. Cl.
USPC ..... Plt./102

(58) Field of Classification Search
USPC ..... Plt./101, 102, 107, 123, 128, 130, 137, Plt./141, 148, 132, 143
See application file for complete search history.

(56) References Cited

PUBLICATIONS

Prweb Tesselaar Plants Introduces SweetSpot Roses—The Decorator Rose Sep. 12, 2013, retrieved on Dec. 3, 2015, retrieved from the Internet at <http://www.prweb.com/releases/2013/9/prweb11114553.htm> 4 pp.*

* cited by examiner

*Primary Examiner* — June Hwu
(74) *Attorney, Agent, or Firm* — Cassandra Bright

(57) ABSTRACT

A new and distinct *Rosa* cultivar, for garden use named 'IntRos01' is disclosed, characterized by abundant flowering, compact plant form and unique flower coloration of intense pink with a large yellow blotch surrounding a smaller dark red blotch. The new variety is a *Rosa*, normally produced as an outdoor garden or container plant.

3 Drawing Sheets

Latin name of the genus and species: *Rosa hybrida.*
Variety denomination: 'IntRos01'.

BACKGROUND OF THE INVENTION

The new *Rosa* cultivar is a product of a planned breeding program conducted by the inventor, Robert Ilsink, in Leersum, Netherlands. The objective of the breeding program was to produce new *Rosa* varieties for ornamental commercial applications. The cross resulting in this new variety was made during April of 2006.

The seed parent is the unpatented, proprietary variety referred to as *Rosa* 'B407-03'. The pollen parent is the unpatented, proprietary variety referred to as *Rosa* 'B213-04'. The new variety was discovered in April of 2007 by the inventor in a group of seedlings resulting from the 2006 crossing, in a research greenhouse in Leersum, Netherlands.

Asexual reproduction of the new cultivar was performed by terminal semi-soft wood vegetative cuttings. This was first performed at a research greenhouse in Leersum, Netherlands in Summer of 2008 and has shown that the unique features of this cultivar are stable and reproduced true to type in successive generations.

SUMMARY OF THE INVENTION

The cultivar 'IntRos01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IntRos01'

These characteristics in combination distinguish 'IntRos01' as a new and distinct *Rosa* cultivar:

1. Intense pink flower with a large yellow blotch surrounding a smaller dark red blotch.
2. Compact size.
3. Abundant flowering.

Plants of the new cultivar 'IntRos01' are similar to plants of the seed parent, *Rosa* 'B407-03' in most horticultural characteristics, however, plants of the new cultivar 'IntRos01' differ in the following:

1. Intense pink flower with a large yellow blotch surrounding a smaller dark red blotch. The seed parent has a pink colored flower.
2. Approximately 10 petals per flower. The seed parent has approximately 25 petals per flower.

Plants of the new cultivar 'IntRos01' are similar to plants of the pollen parent; *Rosa* 'B213-04' in most horticultural characteristics, however, plants of the new cultivar 'IntRos01' differ in the following;

1. Intense pink flower with a large yellow blotch surrounding a smaller dark red blotch. The pollen parent has a pink colored flower.
2. Approximately 10 petals per flower. The pollen parent has approximately 5 petals per flower.

COMMERCIAL COMPARISON

Plants of the new cultivar 'IntRos01' can also be compared to the commercial variety *Rosa* 'Interbylonbab', unpatented. These varieties are similar in most horticultural characteristics; however 'IntRos01' differs in the following:

1. Flower color is intense pink with a large yellow blotch surrounding a smaller dark red blotch. Comparator is pink with a slight yellow tint.
2. Less compact, more upright form. The comparator is more compact and more spreading in form.

BRIEF DESCRIPTION OF THE PHOTOGRAPHS

The accompanying photograph in FIG. 1 illustrates in full color a typical plant of 'IntRos01' grown outdoors, in an approximately 2 gallon nursery pot. Age of the plant photographed is approximately 2 years.

Figure 1:
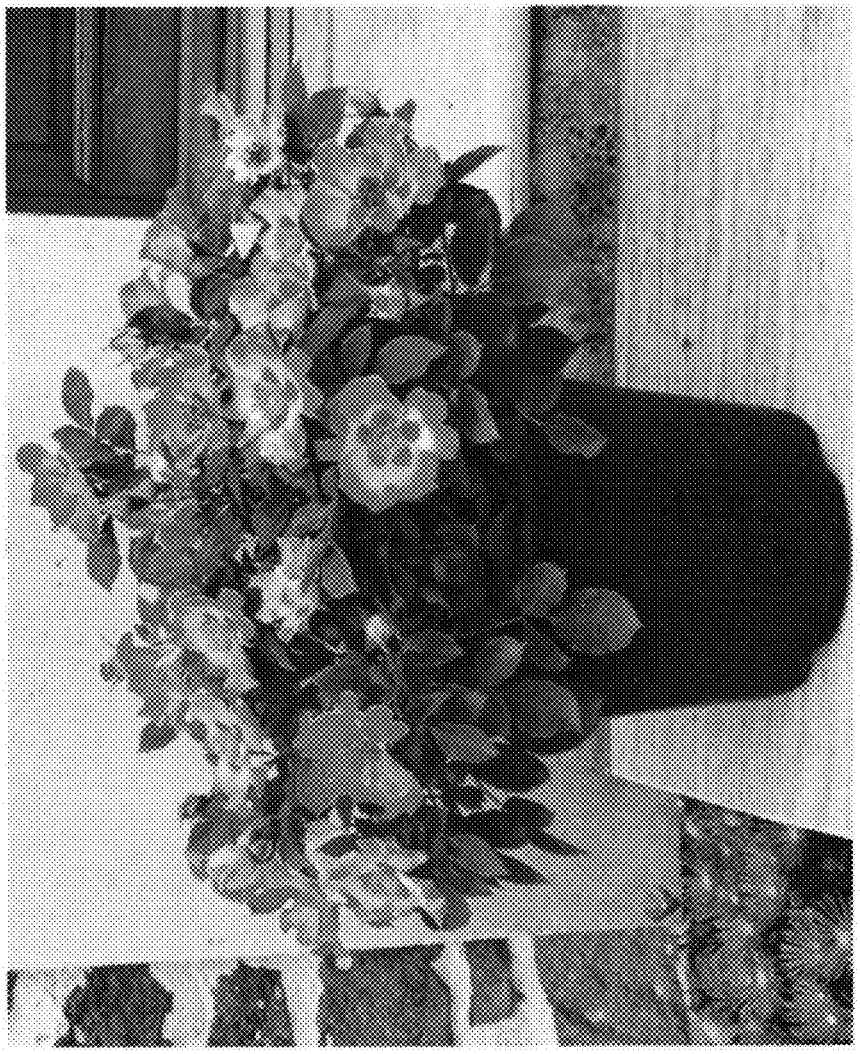
Figure 2:
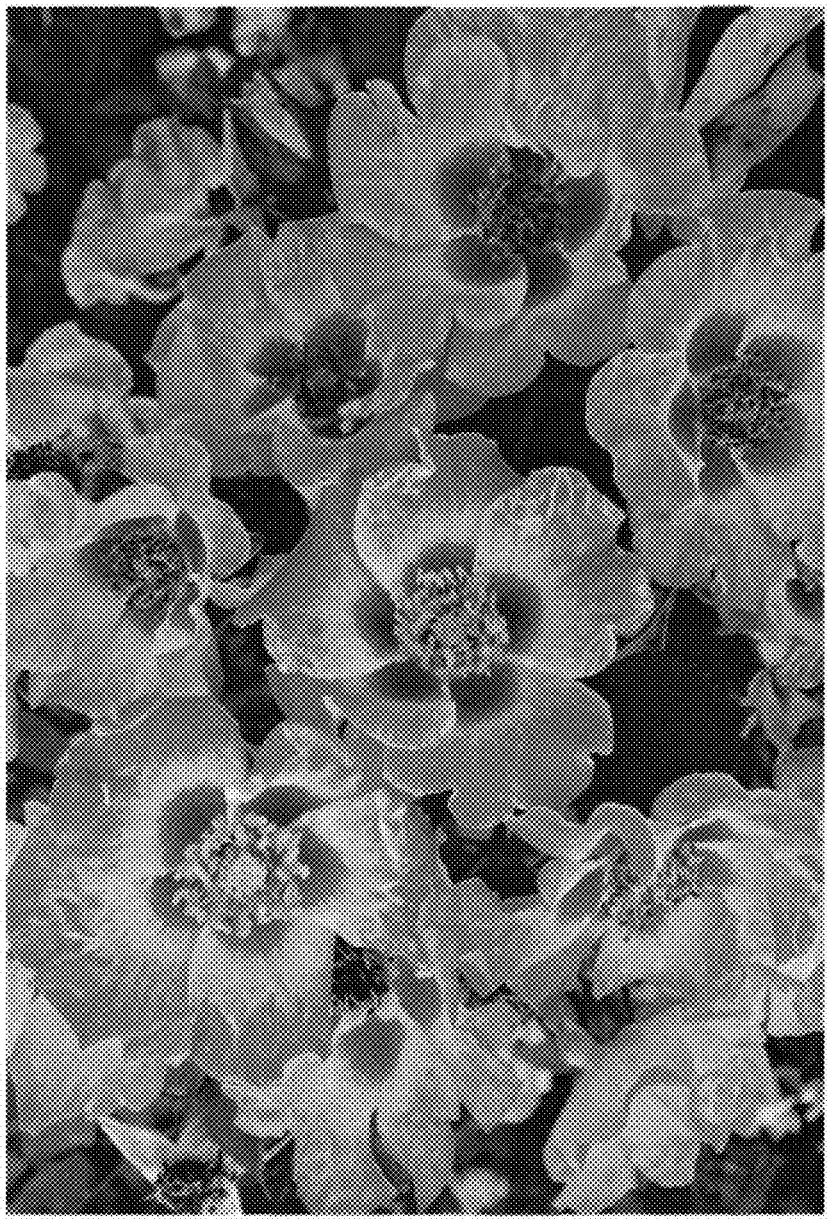
FIG. 2 illustrates a close up of multiple flowers, in various stages of maturity.
Figure 3:
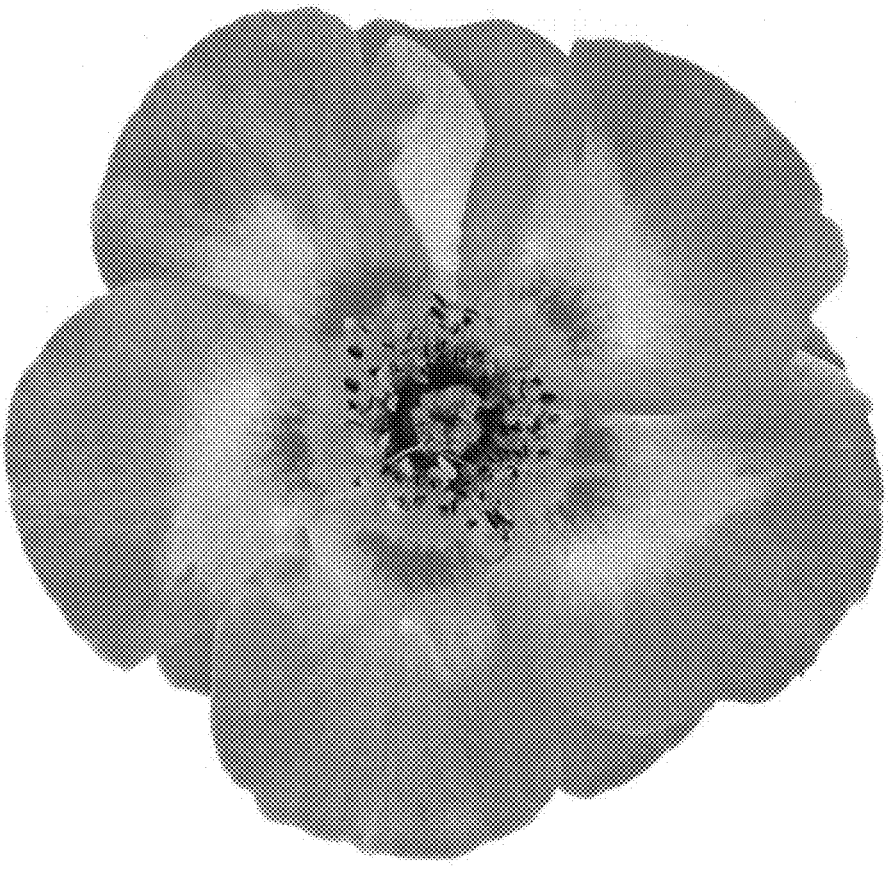
FIG. 3 illustrates a close up of a single mature flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'IntRos01' plants grown outdoors, in Leersum, Netherlands. The growing temperature ranged from approximately 0° C. to 28° C. during the day and from approximately −5° C. to 18° C. during the night. General light conditions are bright, normal sunlight. Measurements and numerical values represent averages of typical plant types.

Botanical classification: *Rosa hybrida* 'IntRos01'.

Commercial classification: Shrub rose.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Compact spreading.

In a container or in the ground: In container.

Height: 600 mm (60 cm).

Plant spread: 500 mm (50 cm).

Rootstock: Own root.

Growth rate: Approximately 2 years to reach 0.6 meters.

Branching characteristics: Sympodial branching.

Length of primary lateral branches: Approximately 60 cm.

Diameter of lateral branches: Approximately 1 cm.

Quantity of lateral branches: Numerous.

Branching arrangement: Branching from every axillary bud possible.

Branches—young wood:

*Diameter*.—Approximately 0.5 cm.

*Texture*.—Herbaceous; glossy with weak anthocyanin coloration.

*Approximately density/quantity of thorns*.—Highly variable, from sparse to moderately dense. No typical pattern of density observed.

*Color*.—Near Red-Purple RHS 70A.

Branches—old wood:

*Diameter*.—Approximately 1 cm, after 2 years.

*Color*.—Near Green RHS 141B.

*Texture*.—Woody; semi glossy.

*Approximately density/quantity of thorns*.—Highly variable, from sparse to moderately dense. No typical pattern of density observed.

*Color of thorns*.—Red purple, closest to 59A.

*Size and shape of thorns*.—Narrow, needlelike thorns, approximately 2 to 3 mm at base and 1 mm at apex.

FOLIAGE

Leaf:

*Arrangement*.—Alternate.

*Quantity*.—Approximately 8 per main branch.

*Average length*.—Approximately 12 cm.

*Average width*.—Approximately 8 cm.

Leaflet:

*Quantity*.—Approximately 7 per leaf.

*Average length*.—Approximately 4 cm.

*Average width*.—Approximately 2.5 cm.

*Shape of blade*.—Oval.

*Apex*.—Pointed.

*Base*.—Rounded.

*Margin*.—Serrated.

*Appearance of top surface*.—Semi glossy.

*Appearance of bottom surface*.—Matte.

*Texture of top surface*.—Non-pubescent.

*Texture of bottom surface*.—Non-pubescent.

*Leaf internode length*.—Average 5 cm.

*Color*.—Young foliage upper side: Near Green RHS 133B. Weak anthocyanin coloration along margin near Greyed-Red 180A. Young foliage under side: Near Green RHS 133B. Weak anthocyanin coloration along margin near Greyed-Purple 183A. Mature foliage upper side: Near Green RHS 126A. Weak anthocyanin coloration along margin near Greyed-Purple 187A. Mature foliage under side: Near Green RHS 126A. Weak anthocyanin coloration along margin near Greyed-Purple 187A.

*Venation*.—Type: Reticulate. Venation color upper side: Indistinguishable from leaf blade. Venation color under side: Indistinguishable from leaf blade.

Petiole:

*Average length*.—Approximately 2.5 to 3.5 cm.

*Average diameter*.—Approximately 0.3 cm.

*Color*.—Near RHS Yellow-Green 144A, in early Spring some flushing of Greyed-Purple 187D.

*Texture*.—Glabrous, occasional irregularly occurring minute spine.

Rachis:

*Average length*.—Approximately 3.4 to 5.5 cm.

*Average diameter*.—Approximately 0.3 cm.

*Texture*.—Glabrous.

*Color*.—Near RHS Yellow-Green 144A, in early Spring some flushing of Greyed-Purple 187C.

FLOWER

Natural flowering season: Spring until Autumn.

Begins flowering after how many years/months: As early as 2 months from a rooted liner.

Inflorescence type and habit: Raceme of single or semi-double flowers. Under low light conditions, a single whorl of 5 petals is formed. Under high light conditions, 10 to 15 petals make up a semi-double flower.

Rate of flower opening: Approximately 1 day from bud to fully opened flower.

Flower longevity on plant: 4 days, after fully opened.

Quantity of flowers: 3-15 per inflorescence.

Inflorescence size:

*Diameter*.—Approximately 18 cm.

*Length*.—Approximately 20 cm.

Individual flower size:

*Diameter*.—Approximately 4.3 to 5.5 cm.

*Depth*.—Approximately 2.0 cm.

Peduncle:

*Length*.—3 cm.

*Diameter*.—0.2 cm.

*Texture*.—Glabrous.

*Color*.—Near RHS Green 143C.

Pedicel:

*Length*.—Average range 1.3 to 3.0 cm.

*Diameter*.—0.2 cm.

*Texture*.—Glabrous.

*Color*.—Near RHS Green 143C.

Petals:

*Petal arrangement*.—Rotate, overlapping.

*Size*.—Medium.

*Length*.—2 cm.

*Width*.—2 cm.

*Shape*.—Broad ovate.

*Margin*.—Weak reflexing of margin, minutely lobed. Irregularly occurring incision, typically 0 to 3 per petal, approximately 0.7 deep.

*Apex*.—Undulating, obtuse to shallow lobed.

*Base*.—Obtuse.

*Petal quantity*.—Average 10.

*Texture*.—Medium strong.

Color:

*Petals: when opening*.—Upper surface: Near RHS Red 50A, but brighter, large interior yellow blotch near Yellow 9A, Basal blotch near Red 45C, base near Yellow 9A. Lower surface: Near RHS Red-Purple 58B, with Yellow streaking near 9B.

*Fully opened*.—Upper surface: Near RHS Red-Purple N57B, large center blotch near Yellow 13A. Inside large blotch a smaller blotch near Red 53B. Base near Yellow 9A. Some Yellow streaking from blotch into Red-Purple outer section, colored near yellow 13A. Lower surface: Near Red-Purple RHS 73B, streaked with yellow 9A. Color Changes when aging: Near RHS Red-Purple N57C, flushed with Violet 84B. Large blotch near Red-Purple 73D, smaller blotch changes to faint streaks near Red 53B.

Bud:

*Shape*.—Round.

*Length*.—Approximately 1.5 cm.

*Diameter*.—Approximately 1 cm.

*Color*.—Near Red-Purple RHS 73B near apex, near yellow 9B, lower section.

Sepals:

*Length*.—1 cm.

*Width*.—0.4 cm.

*Shape*.—Narrow deltoid.

*Color*.—Interior Surface: Near RHS Green 136A. Exterior Surface: Near RHS Green 136A.

*Texture*.—Non pubescent, matte.

Sepal extensions: Medium to strong.

Quantity: Average 5 per flower.

Receptacle:

*Length*.—0.7 cm.

*Width*.—0.7 cm.

*Shape*.—Flattened dome.

*Color*.—Near RHS Green 143C.

Fragrance: None.

REPRODUCTIVE ORGANS

Stamens:

*Number*.—Average range 70 to 90.

*Filament length*.—Approximately 0.3 cm.

*Filament color*.—Yellow 9A.

Anthers:

*Length*.—0.2 cm.

*Shape*.—Linear.

*Color*.—Near Yellow-Orange RHS 20C.

*Pollen*.—Color: Near Yellow RHS 9A. Quantity: Abundant.

Pistil: Number: Approximately 60. Pistil Length: Approximately 1.0 cm.

*Style*.—Length: Approximately 0.2 cm. Color: Near Yellow-White RHS 158B.

*Stigma*.—Shape: Linear. Color: Near Yellow-White RHS 158B.

OTHER CHARACTERISTICS

Seeds and fruits: Not observed to date. Fruits typically dry up, without fully forming.

Disease/pest resistance: Good overall disease resistance to normal pests and diseases typical of garden roses.

What is claimed is:

1. A new and distinct cultivar of *Rosa* plant named 'IntRos01' as herein illustrated and described.

* * * * *